United States Patent [19]
Philo et al.

[11] Patent Number: 5,108,896
[45] Date of Patent: Apr. 28, 1992

[54] SIMULTANEOUS IMMUNOASSAY OF TWO ANALYTES USING DUAL ENZYME LABELLED ANTIBODIES

[75] Inventors: Roger D. Philo, Guilford Surrey; Gerald J. Allen, Windlesham Surrey, both of England

[73] Assignee: Applied Research Systems ARS Holding N.V., Curacao, Netherlands Antilles

[21] Appl. No.: 20,462

[22] Filed: Mar. 2, 1987

[30] Foreign Application Priority Data

Mar. 21, 1986 [GB] United Kingdom ............... 8607101

[51] Int. Cl.$^5$ .......................................... G01N 33/535
[52] U.S. Cl. .................................. 435/7.5; 435/7.92; 435/973; 435/975; 436/500; 436/518
[58] Field of Search ................... 435/7, 14, 18, 19, 21, 435/810, 7.5, 7.92; 436/518, 536, 538, 540, 543, 544, 808, 500

[56] References Cited

U.S. PATENT DOCUMENTS 4,690,890 9/1987 Loor et al. ................ 435/240.27 X Primary Examiner—Esther M. Kepplinger
Attorney, Agent, or Firm—Stephan P. Williams

[57] ABSTRACT

The present invention relates to dual analyte enzyme immunoassays for assaying two antigens in a single liquid sample wherein the two immunoreactions are carried out simultaneously and wherein subsequently the two enzyme reactions occur simultaneously. Suitable enzyme/substrate pairs are beta-galactosidase/nitrophenyl-beta-D-galactoside (p- an/or o-) and alkaline phosphatase/phenolphthalein monophosphate.

28 Claims, 10 Drawing Sheets

SIMULTANEOUS IMMUNOASSAY OF TWO ANALYTES USING DUAL ENZYME LABELLED ANTIBODIES

BACKGROUND OF THE INVENTION

The present invention relates to methods of immunoassay of antigens and to kits for carrying out such methods. In particular, it relates to methods of immunoassay employing enzyme labels (hereinafter referred to as enzyme immunoassays) whereby two antigens are assayed simultaneously in a single sample.

The term "antigen" as used herein will be understood to include both permanently antigenic species (for example proteins, peptide hormones, bacteria, bacteria fragments, cells, cell fragments and viruses) and haptens which may be rendered antigenic under suitable conditions (including, for example, narcotics, hypnotics, analgesics, cardiovascular drugs, vitamins, non-peptide hormones and metabolites thereof, antibiotics, pesticides and sugars).

Radioimmunoassays which can simultaneously measure two different analytes in a single sample have been available for several years. The principle of these dual analyte or "combo" assays is that two conventional assays are performed simultaneously in the same reaction vessel, with the two component assays using different radionuclide labels which can be distinguished from one another by their different energy levels. Suitable pairs of radionuclides which have been employed include $^{125}I/^{131}I$ and $^{125}I/^{57}Co$. Such dual radioimmunoassays offer significant benefits in terms of convenience, speed of obtaining results, laboratory throughput etc. and have become widely accepted in those areas where it is routine practice to measure two analytes in a single sample (e.g. vitamin $B_{12}$ and folate for the differential diagnosis of certain anaemias). However, these assays suffer from the same inherent disadvantages as all assays using short-lived radionuclides as labels. These include short shelf-life, exposure of the user to radiation, the requirement for special facilities and problems with disposal of waste.

The use of non-radioactive labels overcomes these problems and currently enzyme labels are the most commonly used replacement for immunoassays. For enzymes to be used in "combo" assays, it is necessary to identify two suitable enzyme-substrate pairs which not only fulfil the criteria necessary for enzyme immunoassays (ability to be conjugated to one of the reactants with little or no loss of enzyme or immunological activity, freedom from interference by the sample or assay conditions etc) but which, under certain conditions, do not interact with one another during the immunoreaction and can simultaneously catalyse separate substrate conversions to generate products which can be measured independently of one another, either by direct monitoring of their production or by monitoring removal of substrate during the incubation period.

Blake et. al. in Clinical Chemistry (1982) 28 1469–1473 reported the development of a dual analyte enzyme immunoassay for the two haptenic hormones thyroxine ($T_4$) and triiodothyronine ($T_3$), involving the use of alkaline phosphatase and $\beta$-galactosidase as the enzyme labels and phenolphthalein monophosphate and o-nitrophenyl-$\beta$-galactoside (o-NPBG) as the respective substrates. In this assay, firstly unlabelled $T_3$ and $T_4$ compete respectively with $T_3$-$\beta$-galactosidase conjugate and $T_4$-alkaline phosphatase conjugate for binding to an antibody reagent comprising $T_3$ and $T_4$ specific antibodies. The bound fractions of the two enzyme labels are separated by a second antibody precipitation and, after washing, the precipitate is resuspended in an enzyme substrate solution containing phenolphthalein monophosphate and o-nitrophenyl-$\beta$-galactoside. The amounts of the two enzyme labels are then determined sequentially in a two-stage incubation protocol, the amount of $\beta$-galactosidase being initially determined by monitoring the absorbance of o-nitrophenol at 420 nm and the pH then being raised to determine the amount of alkaline phosphatase by monitoring the absorbance at 540 nm. Since the two enzyme reactions are performed sequentially rather than simultaneously, this assay is not a true "combo" immunoassay. We have now found, however, that it is in fact feasible to perform true "combo" immunoassays employing two enzyme labels.

SUMMARY OF THE INVENTION

According to one aspect of the present invention, we therefore provide a dual analyte enzyme immunoassay for assaying two antigens in a single liquid sample wherein the two immunoreactions are carried out simultaneously and wherein subsequently the two enzyme reactions occur simultaneously.

The enzyme labels (and hence indirectly the antigens) can be quantified by direct monitoring of the products of the enzyme-catalysed substrate conversions. Alternatively, the enzyme labels could be quantified by monitoring removal of substrate during the incubation period.

DETAILED DESCRIPTION OF THE INVENTION

Alkaline phosphatase and $\beta$-galactosidase are currently particularly preferred for use as labels in conventional enzyme immunoassays, primarily because they can be readily linked to other proteins, e.g. antibodies, without substantial loss of activity and catalyze reactions which give rise to coloured products. We have found that, under certain conditions, it is possible to perform true "combo" enzyme immunoassays using alkaline phosphatase and $\beta$-galactosidase as the two enzyme labels.

The optimum pH for hydrolysis of phenolphthalein monophosphate by alkaline phosphatase is 9.8. In the presence of a high concentration (e.g. about 1M) of diethanolamine, the pH can, however, be reduced to 8.6 with no loss of activity.

$\beta$-galactosidase has a pH optimum of 7.4 for p-nitrophenyl-$\beta$-D-galactoside (p-NPBG), although in a single assay format using normal substrate concentrations (up to approximately 5 mM), the pH can be raised to 8.6 with only a slight loss (approximately 20%) of activity. However, we have found that in the same assay system, but containing about 1M diethanolamine, the activity of β-galactosidase is almost totally abolished. The kinetics of inhibition of β-galactosade by diethanolamine are complex, but the major effect is a competitive one with the Michaelis constant (Km) of β-galactosidase for p-NPBG in the presence of 1M diethanolamine being altered from 66 μm to 21 mM. We have also found, however, that by increasing the concentration of p-NPBG at pH 8.6, even in the presence of about 1M diethanolamine, substantial activity of β-galactosidase can be achieved. Substantial activity of β-galactosidase is also obtained if the same reaction medium is used but with p-NPBG replaced by o-NPBG.

Thus, in a preferred embodiment of an immunoassay according to the present invention, the enzyme/substrate pairs β-galactosidase /nitrophenyl-β-D-galactoside (p- and/or o-) and alkaline phosphatase/phenolphthalein monophosphate are employed in the enzyme reaction step at a suitable pH and in the presence of diethanolamine, the concentration of nitrophenyl-β-D-galactoside being sufficient to substantially offset inhibition of β-galactosidase by the diethanolamine, such that the two enzyme reactions proceed simultaneously.

The conversion of phenolphthalein monophosphate to phenolphthalein by alkaline phosphatase may be monitored by measurement of absorbance at 554 nm, while the conversion of p-NPBG to p-nitrophenol or o-NPBG to o-nitrophenol by β-galactosidase may be monitored by measurement of absorbance at 404 nm, a correction being made for the low absorbance of phenolphthalein at this wavelength.

The products of the two concurrent enzyme reactions may be monitored simultaneously using a diode array spectrophotometer, but in a conventional spectrophotometer the O.D. measurements at 404 nm and 554 nm must necessarily be separated.

Generally, the concurrent enzyme reactions will be carried out at a pH between 7 and 10. The concentration of diethanolamine present in the enzyme reaction medium may be adjusted to balance the signals obtained from the two enzymes as reducing the diethanolamine concentration will decrease alkaline phosphatase activity and increase the activity of β-galactosidase and increasing the concentration of diethanolamine will have the opposite effects. Generally, the concentration of diethanolamine employed will be in the range 0.25M to 1M. The signals may also be balanced by adjusting the pH of the reaction medium either to favour alkaline phosphatase activity at a pH greater than 8.6 or to favour β-galactosidase activity at a pH less than 8.6. The pH will however preferably be between 8.5 and 8.7.

It is preferable to estimate the activities of the two enzymes using substrate concentrations at least five times the Km of the corresponding enzyme so that any small variations in substrate concentration do not significantly affect the rate of the enzyme-catalysed reaction. It is most preferred to employ p-NPBG as the substrate for the β-galactosidase label, preferably at a concentration of about 50 mM. Thus, for example, the amounts of the two labels removed from the assay mixture in the separation step may be conveniently determined by incubation in the presence of a substrate buffer solution at a pH of about 8.6 initially comprising 0.25M to 1M diethanolamine, 3-10 mM phenolphthalein monophosphate and about 50 mM p-nitrophenyl-β-D-galactoside.

In such an immunoassay, either whole antibodies may be employed or at least one of the antibody reagents may comprise fragments of antibodies having an antigen binding-site. It will be understood that the term "antibody" as used herein includes within its scope:

a) any of the various classes or sub-classes or immunoglobulin, e.g. IgG or IgM, derived from any of the animals conventionally used e.g. sheep, rabbits, goats or mice;
b) monoclonal antibodies; and
c) fragments of antibodies, monoclonal or polyclonal, the fragments being those which contain the binding region of the antibody, i.e. fragments devoid of the Fc portion (e.g. Fab, Fab', F(ab')$_2$) or the so-called "half-molecule" fragments obtained by reductive cleavage of the disulphide bonds connecting the heavy main chain components in the intact antibody. The methods for preparation of antigen-binding fragments of antibodies are well-known in the art and will not be described herein. The techniques for preparing monoclonal antibodies are also well-known (see, for example Galfre G. & Milstein C. (1981). "Preparation of Monclonal Antibodies: Strategies and Procedures" in Methods in Enzymology 73, 1-46).

Immunoassays of the present invention are particularly advantageous for assaying pairs of antigens which are found together in physiological samples e.g. human serum samples or urine samples obtained from healthy or diseased patients. Such enzyme immunoassays are, for example, desirable for assaying pairs of hormones including, for example, $T_4$ (thyroxine)/$T_3$ (triiodothyronine), LH (lutenising hormone)/FSH (follicle-stimulating hormone) and $T_4$/TSH (thyroid-stimulating hormone).

A dual analyte enzyme immunoassay according to the present invention may, for example, comprise two simultaneous 1-site enzyme immunometric assays, preferably of the indirect-link type disclosed in our co-pending published European patent application no. 177 191 (hereinafter referred to as a 1-site IEMA), two simultaneous 2-site enzyme immunometric assays, preferably of an indirect-link type analogous to the radioimmunometric assay described in our co-pending European published patent application no. 105714 (hereinafter referred to as a 2-site IEMA), or a 1-site enzyme immunometric assay simultaneous with a 2-site enzyme immunometric assay. β-galactosidase and alkaline phosphatase may be conveniently conjugated to antibodies for use in such dual analyte enzyme immunoassays by means of a heterobifunctional reagent [see for example (Ishikawa et al. in J. Immunoassay 4, 209-327 (1983).

A 1-site enzyme immunometric assay is suitable for assaying an antigen having one or more epitopes. In a conventional 1-site enzyme immunometric assay, the antigen under assay (hereinafter referred to as the "ligand") competes with a ligand analogue (i.e. a reagent having the same complexing characteristics as the ligand, the term "ligand analogue" including within its scope a known quantity of the ligand under assay) for enzyme-labelled antibody and, after completion of the complexing reaction, ligand analogue with bound labelled antibody is separated from the assay mixture. The quantity of ligand analogue which binds with the labelled antibody will be inversely proportional to the amount of ligand present in the sample. Commonly, the ligand analogue is immobilised on a solid support to facilitate the separation step. Following separation of the solid support (together with the ligand analogue and a proportion of the labelled component) from the assay mixture, after the complexing reaction has occurred, the proportion of the labelled component which has become complexed to the ligand analogue is determined and the amount of the ligand thereby calculated.

In an improved 1-site enzyme immunometric assay of the type disclosed in published European application no. 177 191, the ligand analogue is not bound directly to the solid support. Instead, the ligand analogue is conjugated with a reagent X, e.g. a hapten such as fluorescein isothiocyanate (FITC), and the solid phase has conjugated to it a binding partner specific for reagent X. A 1-site IEMA for the haptenic hormone thyroxine ($T_4$), wherein the ligand analogue is $T_4$-FITC, is illustrated schematically in FIG. 1.

A preferred dual analyte enzyme immunoassay according to the present invention wherein the component assays are two 1-site IEMAs will thus comprise incubating a mixture of a) the liquid sample (containing two analyte ligands each with one or more epitopes),
b) one or more populations of alkaline phosphatase-labelled antibody molecules specific for the first analyte ligand,
c) one or more populations of $\beta$-galactosidase-labelled antibody molecules specific for the second analyte ligand,
d) a ligand analogue of the first analyte ligand conjugated with a reagent X (the said reagent not being present as a free reagent in the mixture), and
e) a ligand analogue of the second analtye ligand conjugated with said reagent X;

separating, after a suitable incubation period, the portion containing components (d) and (e) from the mixture by means of a solid phase carrying a binding partner specific for reagent X; incubating the said solid phase or the liquid phase in the presence of p-nitrophenyl-$\beta$-D-galactoside, phenolphthalein monophosphate and 0.25M to 1M diethanolamine at a pH of about 8.6, the concentration of p-nitrophenyl-$\beta$-D-galactoside being sufficient to substantially offset inhibition of $\beta$-galactosidase by the diethanolamine; and monitoring the production of phenolphthalein and p-nitrophenol.

Such a dual enzyme immunoassay may, for example, conveniently be employed to assay simultaneously $T_4$ and $T_3$ in a single sample.

In a conventional 2-site enzyme immunometric assay (commonly referred to as a sandwich enzyme immunoassay), the ligand, which must have two or more epitopes, is insolubilised by reaction with an unlabelled antibody conjugated to a solid phase and reacted with an enzyme-labelled antibody directed to a different (preferably roomly-spaced) epitope of the ligand. The quantity of labelled antibody which becomes immobilised due to the complexing reaction is directly proportional to the amount of ligand present in the sample.

Improved 2-site enzyme immunometric assays of the indirect-link type (2-site IEMAs) employ two soluble antibody reagents directed to different epitopes of the ligand, one soluble antibody reagent comprising enzyme-labelled antibody molecules. The solid phase employed is conjugated to a further reagent which is capable of specifically non-covalently binding the non-labelled antibodies to the ligand. These antibodies may, for example, conveniently be conjugated to a reagent X. The separation step is then achieved by using a solid phase conjugated to a specific binding partner for reagent X. Such an indirect-link type 2-site enzyme immunometric assay is shown diagrammatically in FIG. 2.

A preferred dual analyte enzyme immunoassay according to the present invention wherein the component assays are two 2-site IEMAs comprises incubating a mixture of a) the liquid sample (containing two analyte ligands with more than one epitope),
b) one or more populations of alkaline phosphatase-labelled antibody molecules specific for the first analyte ligand,
c) one or more populations of $\beta$-galactosidase-labelled antibody molecules specific for the second analyte ligand,
d) a reagent comprising antibodies to the first analyte ligand conjugated to a reagent X (the said reagent not being present as a free reagent in the mixture),
e) a reagent comprising antibodies to the second analyte ligand conjugated to said reagent X, and
f) a reagent capable of binding to reagent X by non-covalent binding, but which is not directly bindable to either component (a) or components (b) and (c), the said reagent (f) being bound to a solid phase support;
separating, after a suitable incubation period, the solids fraction from the liquid fraction; incubating the separated solid phase or liquid phase in the presence of p-nitrophenyl-$\beta$-D-galactoside, phenolphthalein monophosphate and 0.25M to 1M diethanolamine at a pH of about 8.6, the concentration of p-nitrophenyl-$\beta$-D galactoside being sufficient to substantially offset inhibition of $\beta$-galactosidase by the diethanolamine; and monitoring the production of phenolphthalein and p-nitrophenol.

An example of a pair of ligands for which such a dual analyte enzyme immunoassay according to the invention is particularly desirable are the hormones LH (lutenising hormone) and FSH (follicle stimulating hormone).

For certain pairs of ligands, e.g. $T_4$ and TSH, it may be particularly desirable to effect a dual analyte enzyme immunoassay according to the invention which consists of a 1-site IEMA simultaneous with a 2-site IEMA. A preferred dual analyte enzyme immunoassay of this type comprises incubating a mixture of a) the liquid sample (containing two analyte ligands, at least one analyte ligand having more than one epitope),
b) one or more populations of alkaline phosphatase-labelled antibody molecules specific for one analyte ligand,
c) one or more populations of $\beta$-galactosidase-labelled antibody molecules specific for the second analyte ligand,
d) a ligand analogue of one of the analyte ligands conjugated with a reagent X (the said reagent not being present as a free reagent in the mixture),
e) a reagent comprising antibodies to the analyte ligand for which component (d) is not a ligand analogue conjugated with said reagent X, the analyte ligand for which reagent (e) is specific having more than one epitope, and
f) a reagent capable of binding to reagent X by non-covalent bonding, but which is not directly bindable to component (a) or components (b) and (c), the said reagent (f) being bound to a solid phase support;

separating, after a suitable incubation period, the solids fraction from the liquid fraction; and determining the amounts of the two enzyme labels in one of the said fractions as hereinbefore described.

By the term "non-covalently bonding" as herein is meant immunological bonding as in an antibody:antigen or antbody:hapten bond or non-immunological bonding such as between a specific binding protein and its ligand, e.g. as in the interaction between Protein A and the $F_c$ portion of an antibody or the interaction between avidin and biotin.

In a preferred dual analyte enzyme immunoassay according to the present invention as hereinbefore described wherein the component assays are two 1-site IEMAs, two 2-site IEMAs or one 1-site IEMA and one 2-site IEMA, it is particularly convenient for the reagent X to be a hapten, for example, selected from fluorescein derivatives (e.g. fluorescein isothiocyanate), rhodamine isothiocyanate, 2,4-dinitrofluorobenzene, phenyl isothiocyanate and dansyl chloride and for the solid phase to be conjugated to an antibody specific for the chosen hapten. Especially preferred as reagent X is FITC in which case anti-FITC antibody is covalently linked to the solid support. An antiserum to FITC may be readily prepared in conventional manner, for example by immunising sheep with FITC conjugated to keyhole limpet haemocyanin. Coupling of the antiserum to the solid support may be affected by, for example, the method of Axen et al. (Nature 214, 1302–1304 (1967)). The use of the binding pair avidin/biotin is also highly preferred. Conveniently, the solid phase may comprise magnetisable particles e.g. magnetisable cellulose particles (see Forrest and Rattle, "Magnetic Particle Radioimmunoassay" in "Immunoassays for Clinical Chemistry", p. 147–162, Ed. Hunter and Corrie, Churchill Livingstone, Edinburgh (1983)).

According to a further feature of the present invention, we provide kits of reagents for carrying out a method of assay according to the invention. Such a kit for a preferred dual analyte enzyme immunoassay as hereinbefore described wherein the component assays are two 1-site IEMAs, two 2-site IEMAs or one 1-site IEMA and one 2-site IEMA, may, for example, comprise appropriate components (b), (c), (d) and (e) and a solid phase carrying a binding partner specific for reagent X.

For convenience of use, two or more of components (b), (c), (d) and (e) may be combined in a single reagent. One or more of these components may be supplied in lyophilized form.

The following non-limiting Examples are intended to illustrate further the present invention.

EXAMPLE 1

A simultaneous dual analyte enzyme immunoassay for LH and FSH wherein the component assays are two indirect link sandwich immunometric assays (i) Preparation of monoclonal antibodies.

Monoclonal antibodies to LH and FSH were obtained from mouse ascites fluid by the process reported by Köhler and Milstein in Nature 256 (1975) 495–497. Antibodies from individual hybridoma cell lines were screened to identify those producing antibody to discrete antigenic determinants. Those antibodies with the highest affinities for the antigens in question were selected for use in the assay.

(ii) Preparation of the antibody reagents (a) anti LH-alkaline phosphatase

One population of monoclonal antibodies to LH was labelled with the enzyme alkaline phosphatase as follows.

0.16 ml N-succinimidyl 4-(N-maleimidomethyl) cyclohexane-1-carboxylate (SMCC) (60 mM in dimethylformamide-DMF) was added to 1.6 ml of alkaline phosphatase (2 mg/ml in 50 mM sodium borate, 1 mM magnesium chloride and 0.1 mM zinc chloride, pH 7.6) and incubated for 1 hour at 30° C. The enzyme was separated by passage through a Sephadex G-25 medium column (1×35 cm) equilibrated in 0.1 M Tris, 1 mM magnesium chloride and 0.1 mM zinc chloride, pH 7.0. The purified enzyme was stored at +4° C. until required.

16.3 $\mu$l of N-succinimidyl 3-(2-pyridyldithio) propionate (SPDP) (25 mM in ethanol) were added to 1 ml of anti-LH monoclonal antibody (3 mg/ml in 200 mM sodium propionate, pH 6.0) and incubated for 30 minutes at room temperature. The antibody was separated by passage through a disposable Sephadex G-25 column (PD-10) equilibrated in 200 mM sodium acetate buffer, pH 4.5. Dithiothreitol (1M) was added to the antibody (1/20 of antibody volume added) and left for 10 minutes at room temperature. The antibody was desalted using a Sephadex G-25 medium column (1×35 cm) equilibrated in 200 mM sodium propionate, pH 6.0.

Antibody and alkaline phosphatase prepared as above were mixed in an equimolar ratio and left to conjugate for 24 hours at 4° C. The resulting conjugate was purified by high-performance liquid chromatography (HPLC) on a TSK 3000 SW column equilibrated in 200 mM sodium propionate, 1 mM magnesium chloride and 0.1 mM zinc chloride at pH 6.0.

(b) Anti-LH-FITC

A second population of monoclonal antibodies directed to a different epitope of LH was labelled with FITC. Conjugation of FITC to this second population of monoclonal antibodies was achieved by reacting 200 $\mu$g of FITC (Sigma London Chemical Co., England) with 5 mg antibody in 1.4 ml sodium bicarbonate buffer, 0.2M, pH 9.0 for 18 hours at room temperature. The reaction mixture was purified by gel filtration on Sephadex G-50 superfine, giving a product incorporating an average of 6 molecules FITC per antibody molecule.

(c) Anti-FSH-$\beta$-galactosidase

150 $\mu$l of SPDP (25 mM in ethanol) was added to 9.4 ml of anti-FSH antibody at 100 $\mu$g/ml in 0.2M sodium propionate buffer at pH 6.0 and incubated at room temperature for 30 minutes. The resulting antibody was then purified by passage down an HPLC TSK 3000 SW column equilibrated in sodium propionate buffer (0.02 M, pH 6.0). The antibody thus obtained was then mixed with an equimolar concentration of $\beta$-galactosidase and incubated overnight at 4° C. before purification on a TSK 4000 column equilibrated in sodium propionate buffer (0.2 M, pH 6.0).

(d) Anti-FSH-FITC

A second population of monoclonal antibodies directed to a different epitope of FSH was conjugated to FITC using the same method as used to prepare the anti-LH-FITC conjugate.

(e) Preparation of 'antibody reagent cocktail'

A 'reagent cocktail' was made consisting of anti-FSH antibody conjugated to β-galactosidase (5 μg/ml), anti-FSH antibody conjugated to FITC (1.25 μg/ml), anti-LH antibody conjugated to alkaline phosphatase (375 ng/ml) and anti-LH antibody conjugated to FITC (250 ng/ml), made up in assay buffer (100 mM Tris/HCl buffer containing 0.5% bovine serum albumin (fraction V), 0.2% sheep serum, 0.2% sodium azide, 100 mM sodium chloride, 1 mM magnesium chloride and 0.1 mM zinc chloride at pH 8.0).

(iii) Preparation of the solid phase reagent

This material comprised anti-FITC polyclonal antibody covalently linked to magnetisable cellulose particles.

Anti-FITC was a conventional polyclonal antiserum obtained by immunising sheep with FITC conjugated to keyhole limpet haemocyanin. The magnetisable cellulose particles were a composite of cellulose containing approximately 50% black ferric(ous) oxide ($Fe_3O_4$), with mean particle diameter of 3 microns (see Forrest and Rattle, "Magnetic Particle Radioimmunoassay", in "Immunoassays for Clinical Chemistry", p. 147-162, Ed. Hunter and Corrie, Churchill Livingstone, Edinburgh (1983)). Anti-FITC antiserum was covalently coupled to the magnetisable cellulose particles following cyanogen bromide activation of the cellulose, according to the procedure of Axen et al. [Nature 214, 1302-1304 (1967)]. The antiserum was coupled at a ratio of 2 ml antiserum to 1 gram of magnetisable solid phase.

The solid phase was diluted to 5 mg/ml in 50 mM Tris/HCl buffer, pH 8.0, containing 0.1% sodium azide, 0.5% bovine serum albumin (BSA), fraction V, 0.25% Tween 20 and 0.5% methocell.

(iv) Preparation of the substrate buffer

The substrate buffer consisted of a 1M solution of diethanolamine containing 150 mM NaCl, 1 mM $MgCl_2$, 3 mM phenophthalein monophosphate and 50 mM p-nitrophenyl-β-D-galactoside at pH 8.6.

(v) Preparation of the stop solution

The stop solution was prepared by adjusting a solution containing 200 mM $Na_2CO_3$, 20 mM $Na_3PO_4$ and 300 mM EDTA to pH 12 and then adding NaOH to 150 mM.

(vi) LH/FSH Assay Protocol

100 μl of sample and 200 μl of antibody reagent cocktail were mixed, vortexed and incubated at 37° C. for 20 minutes after which 200 μl of anti-FITC solid phase (5 mg/ml) was added and vortexed. This was followed by a further 10 minute incubation, then the solid phase was sedimented magnetically and the supernatnent discarded. The magnetic particle solid phase was washed three times by adding 500 μl of wash buffer (10 mM Tris/HCl containing 0.9% sodium chloride at pH 8.6), vortexing and separating magnetically, followed by decanting off the supernatant. After the third wash and decantation step, the solid phase was drained for two minutes. After were incubated at 37° C. for 35 minutes and then 1 ml stop solution was added.

After sedimenting the solid phase magnetically for at least 15 minutes, the concentration of LH was calculated from $A_{554}$ of the supernatant and the concentration of FSH from $A_{404}$ of the supernatant, after correction for absorbance of phenolphthalein at 404 nm.

(vii) Results

Figure 3:
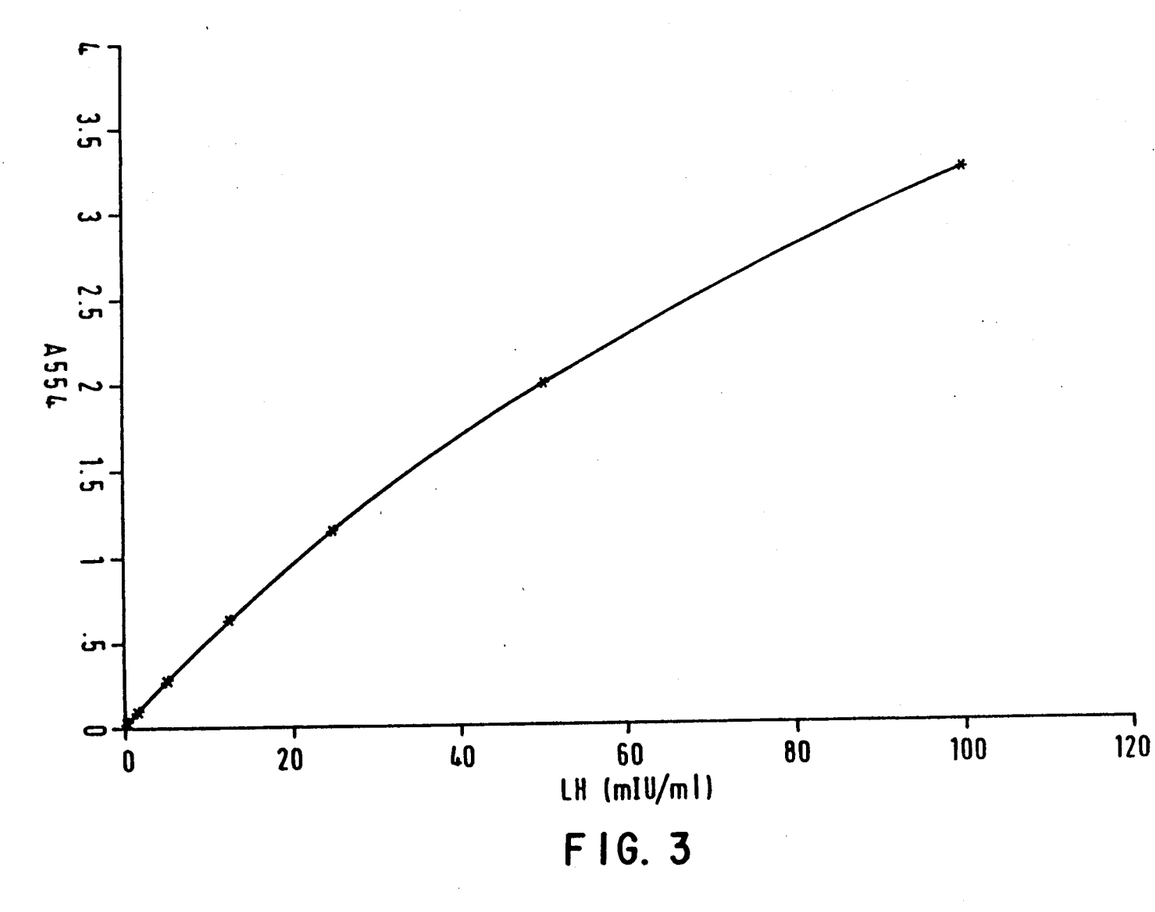
FIGS. 3 and 4 illustrate standard curves for determining LH and FSH in accordance with the present invention.
Figure 4:
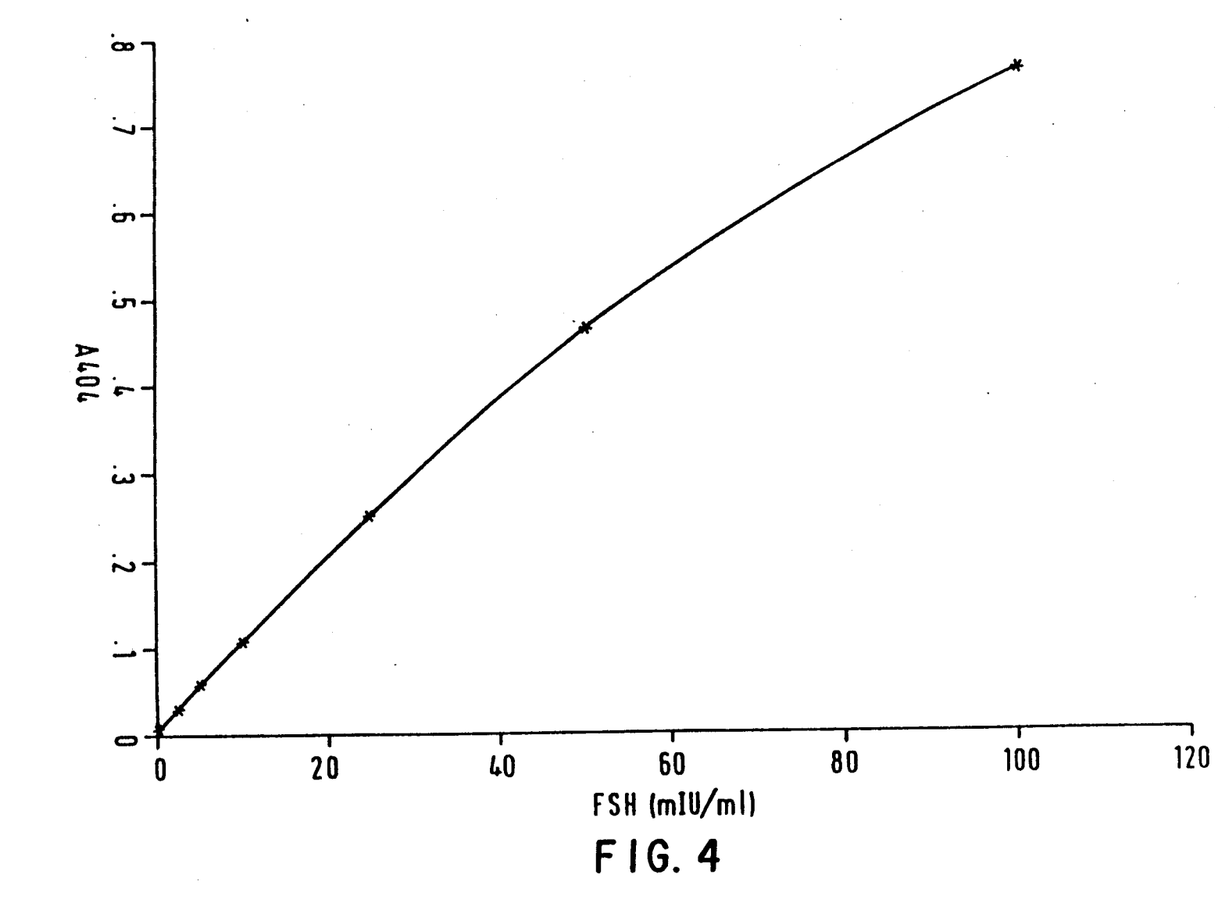

In Table 1 below, the results obtained for samples containing both LH and FSH using the "combo" assay are compared with the results obtained by measuring LH and FSH separately in the same samples using Amerlex RIA kits (Amersham International plc). Standard curves for LH and FSH when determined simultaneously using the "combo" assay are given in FIGS. 3 and 4 respectively.

TABLE 1

| LH (mIU/ml) combo | LH (mIU/ml) Amerlex | FSH (mIU/ml) combo | FSH (mIU/ml) Amerlex |
|---|---|---|---|
| 4.9 | 8.3 | 4.8 | 5.9 |
| 15.3 | 21.8 | 29.5 | 32.0 |
| 29.0 | 36.5 | 67.5 | 66.0 |
| 53.5 | 62.0 | >100.0 | 137.0 |
| >100.0 | 140.0 | >100.0 | 165.0 |
| 2.4 | 2.8 | 1.9 | 2.8 |
| 7.7 | 12.3 | 7.0 | 8.8 |

EXAMPLE 2

A simultaneous dual analyte enzyme immunoassay for $T_4$ and TSH

Figure 1:
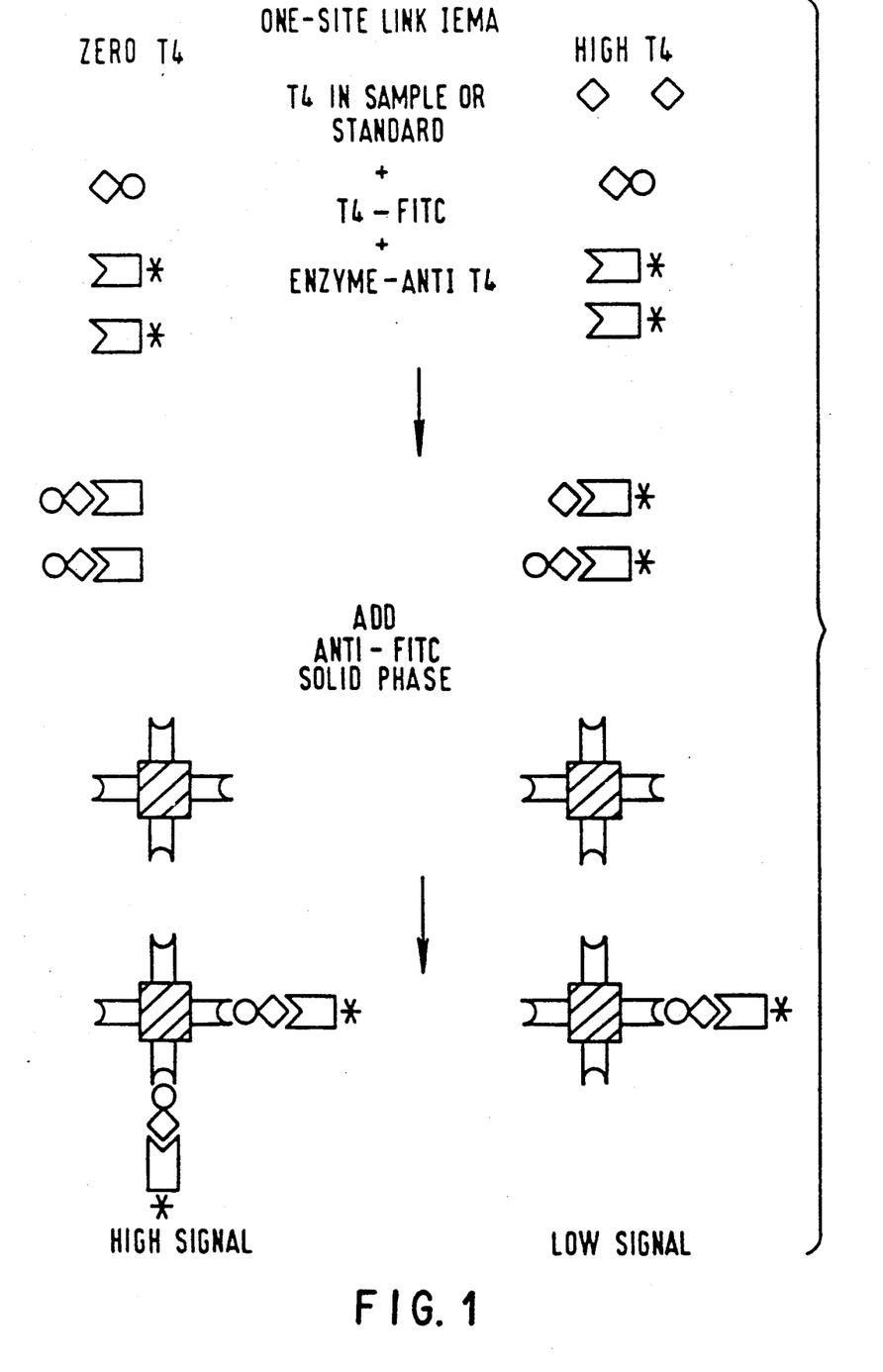
FIG. 1 illustrates a one-site enzyme immunoassay for thyroxine ($T_4$).
Figure 2:
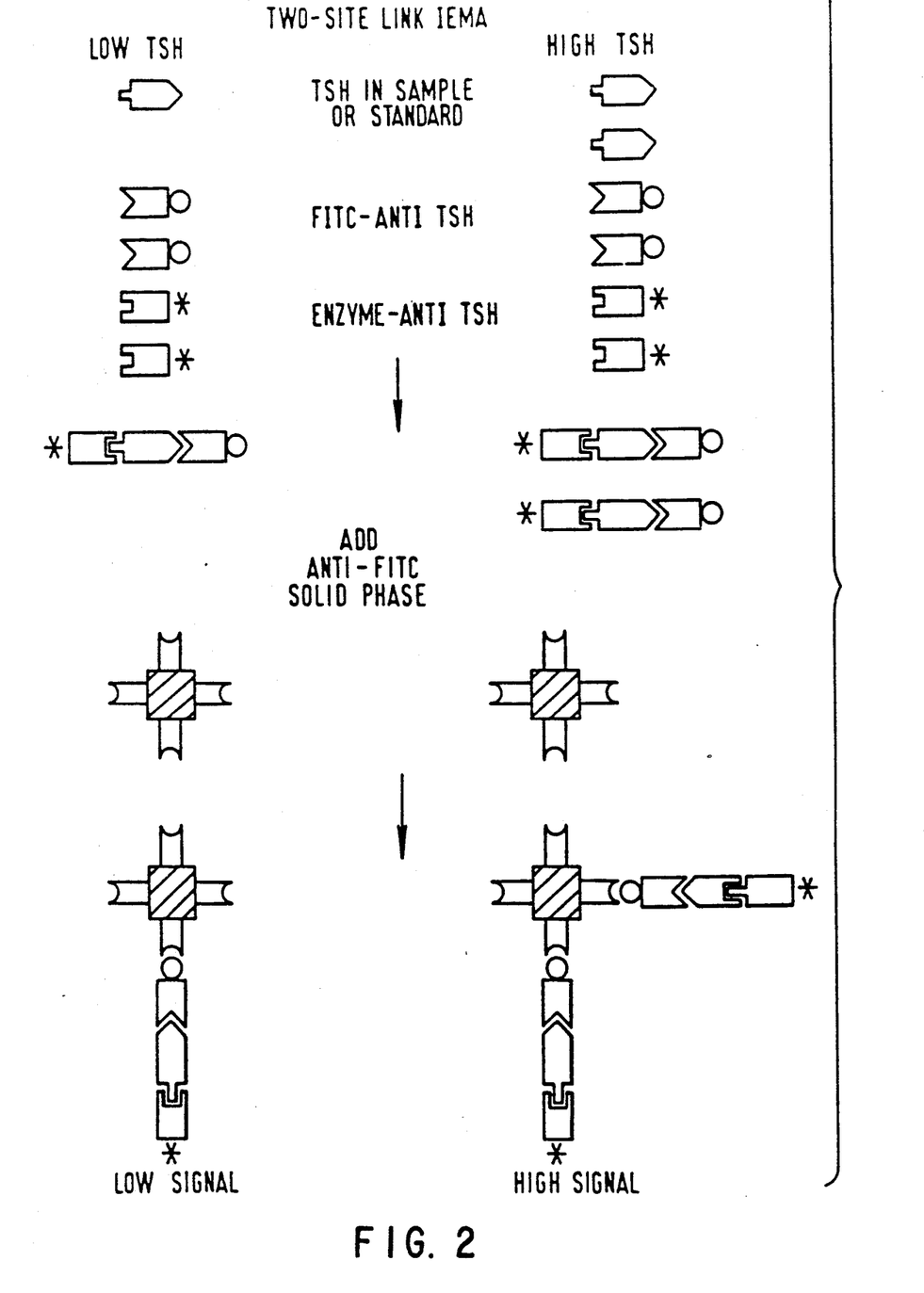
FIG. 2 illustrates a two-site enzyme immunoassay for TSH.

In this Example, a 1-site indirect-link enzyme immunoassay for $T_4$ as illustrated schematically in FIG. 1 was combined with a 2-site indirect-link enzyme immunoassay (i.e. an indirect link sandwich immunoassay) as illustrated schematically in FIG. 2.

(i) Preparation of monoclonal antibodies

Monoclonal antibodies to $T_4$ and TSH were obtained from mouse ascites fluid by the process reported by Kohler and Milstein in Nature 256 (1975) 495-497. Antibodies from individual hybridoma cell lines were screened to identify those producing antibody to discrete antigenic determinants. Those antibodies with the highest affinities for the antigens in question were selected for use in the assay.

(ii) Preparation of antibody reagents

Two populations of monoclonal antibodies directed to different epitopes of TSH were labelled with alkaline phosphatase using the same method as used in Example 1 to prepare the anti-LH-alkaline phosphatase conjugate. Binding of one alkaline phosphatase-labelled monoclonal antibody to TSH did not interfere with the binding of the other enzyme-labelled monoclonal antibody.

A population of monoclonal antibodies to $T_4$ was labelled with β-galactosidase and a further population of anti-TSH monoclonal antibodies, directed to a third epitope of TSH, was conjugated with FITC using the same methods as in Example 1 (ii).

(iii) Preparation of FITC-$T_4$

The conjugate FITC-$T_4$ was prepared and purified by the method of Smith in FEBS Letters 77 25 (1977).

(iv) Preparation of the solid phase reagent

As in Example 1 (iii)

(v) Preparation of the substrate buffer

As in Example 1 (iv)

(vi) Preparation of the stop solution

As in Example 1 (v)

(vii) Preparation of assay reagents

A cocktail of reagents (Reagent A) was prepared consisting of FITC-$T_4$ (10.5 pM), anti-TSH antibody conjugated to FITC (5 μg/ml), anti-TSH antibody conjugated to alkaline phosphatase (1 μg/ml) and 8-anilino-1-napthalene sulphonic acid (1.5 mg/ml) in assay buffer (100 mM Tris/HCl) buffer containing 0.5% bovine serum albumin (fraction V), 0.2% sheep serum, 0.2% sodium azide, 100 mM sodium chloride, 1 mM magnesium chloride and 0.1 mM zinc chloride at pH 8.0).

The second reagent (Reagent B) consisted of anti-$T_4$ antibody conjugated to β-galactosidase (7.61 μg/ml) in assay buffer.

(viii) $T_4$/TSH Assay Protocol

To 100 μl of sample, 200 μl of reagent A and 100 μl of reagent B were added. After vortexing, the assay was incubated at 37° C. for 20 minutes, followed by the addition of 200 μl anti-FITC solid phase (5 mg/ml). After a 5 minute incubation at 37° C., the assay was separated magnetically and the supernatant removed by decantation. The magnetic particle solid phase was washed three times by adding 500 μl of wash buffer (10 mM Tris/HCl containing 0.9% sodium chloride at pH 8.6), vortexing and separating magnetically, followed by decanting off the supernatant. After the third wash and decantation step, the solid phase was drained for two minutes. Upon addition of 300 μl substrate solution, the tubes were incubated at 37° C. for 20 minutes and then 1 ml of stop solution added. The absorbances at 554 and 404 nm were measured after the particles had been sedimented magnetically for at least 15 minutes.

(ix) Results

Results obtained using the $T_4$/TSH "combo" assay to measure $T_4$ and TSH simultaneously in blood serum samples from human hypothyroid, euthyroid and hyperthyroid patients are given in Table 2 below.

TABLE 2

| Patient type | $T_4$ (ng/ml) | TSH (μIU/ml) |
| --- | --- | --- |
| hypothyroid | 79.1 | 9.6 |
| euthyroid | 86.7 | 2.84 |
| hyperthyroid | 108 | 0.784 |

Figure 5:
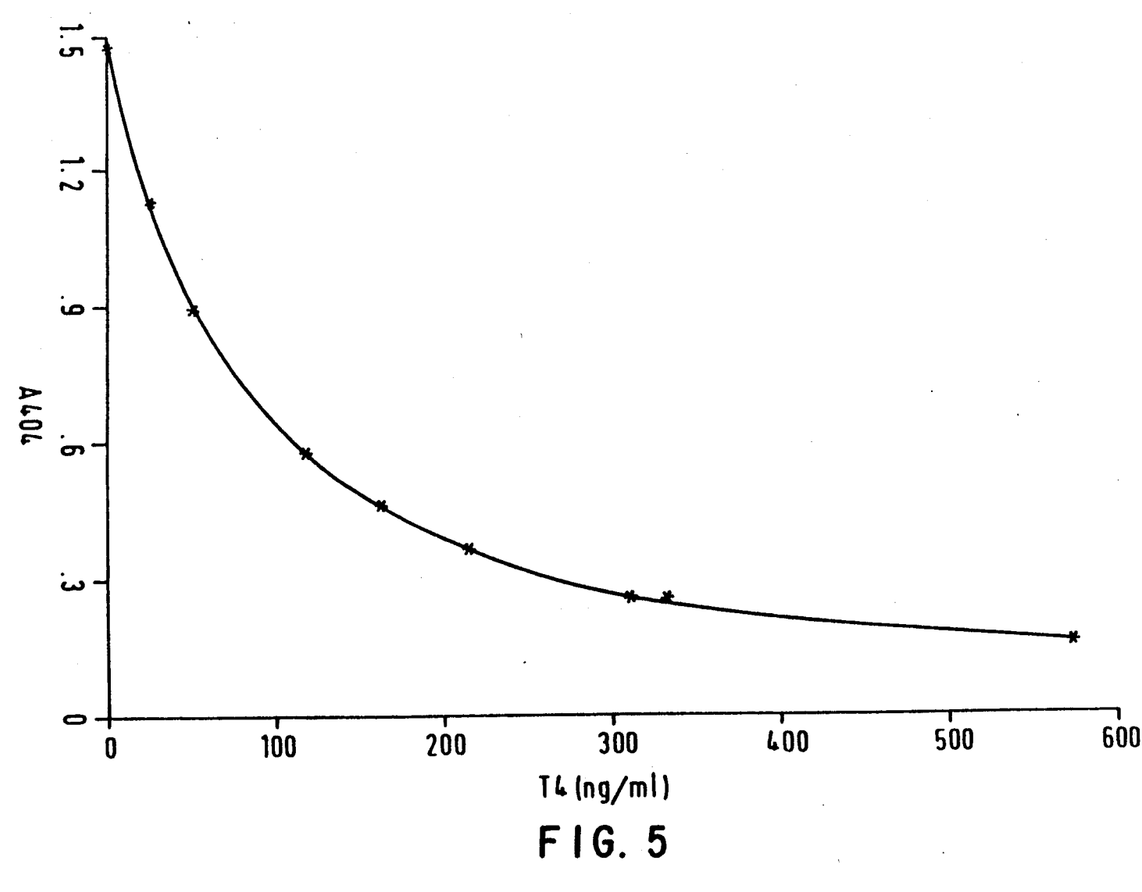
Figure 6:
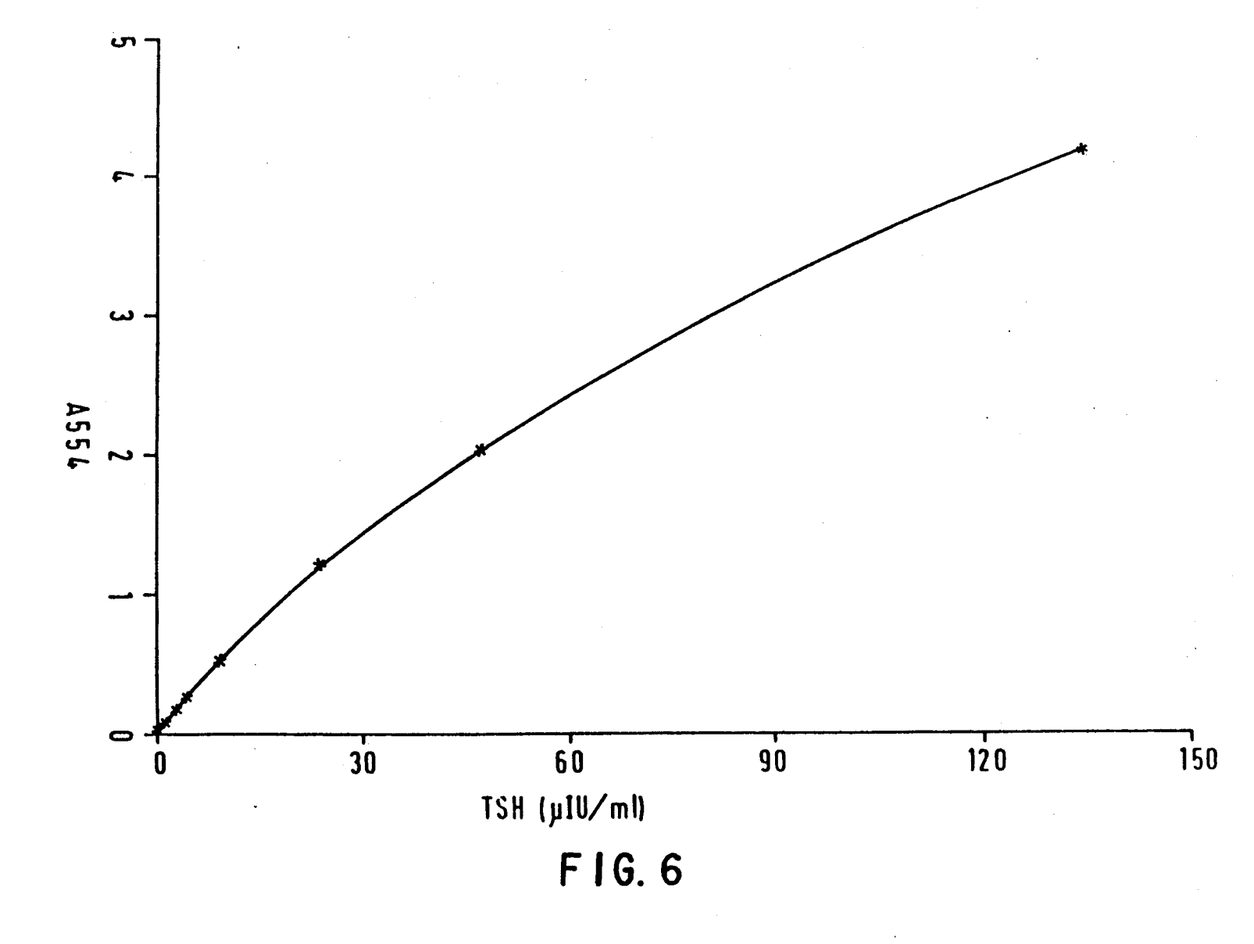

Standard curves for $T_4$ and TSH when determined simultaneously using the "combo" assay are given in FIGS. 5 and 6 respectively.

A further 88 patient samples were assayed for $T_4$ and TSH using the $T_4$/TSH "combo" assay and also separately for $T_4$ using an Amerlex $T_4$ RIA kit (Amersham International plc) and separately for TSH using a 2-site immunoradiometric assay kit (IRMA kit; Serono Diagnostics Limited).

Figure 7:
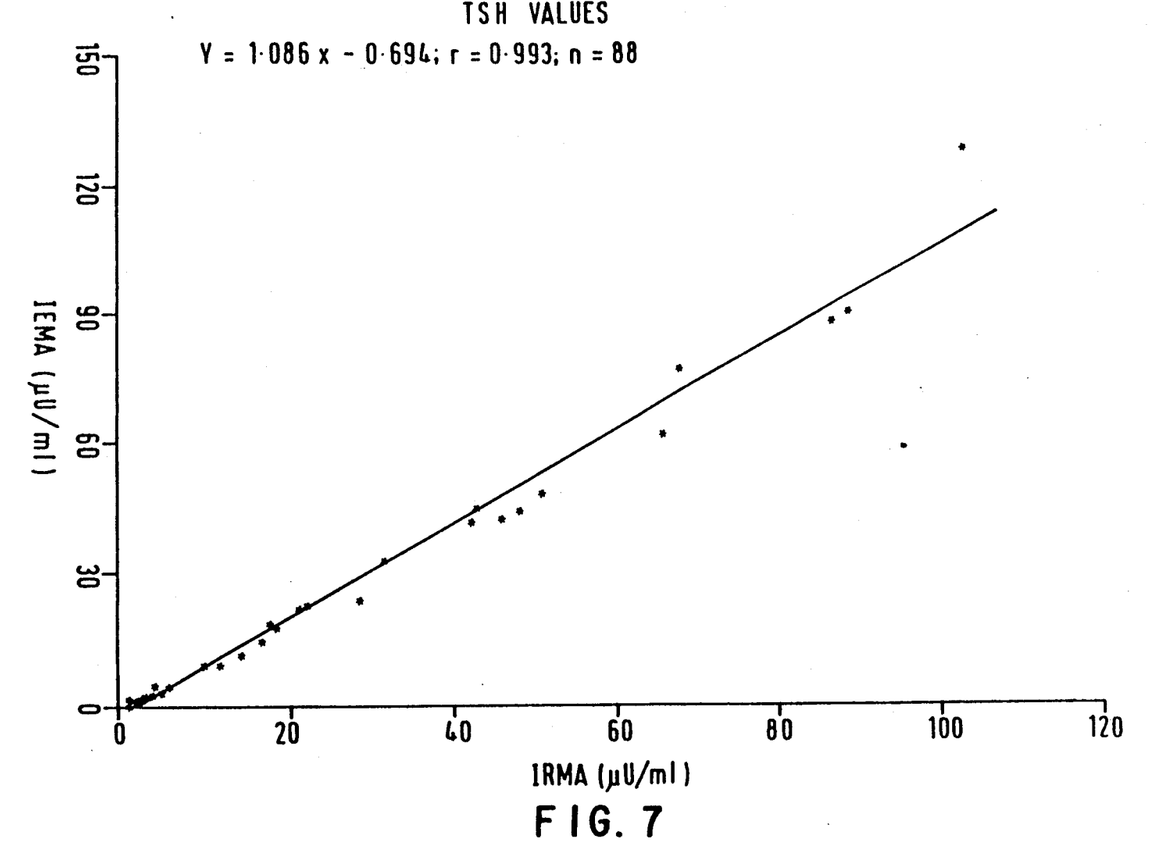
FIGS. 7–9 illustrate a comparison of TSH results determined in accordance with the present invention versus a conventional IRMA assay.
Figure 8:
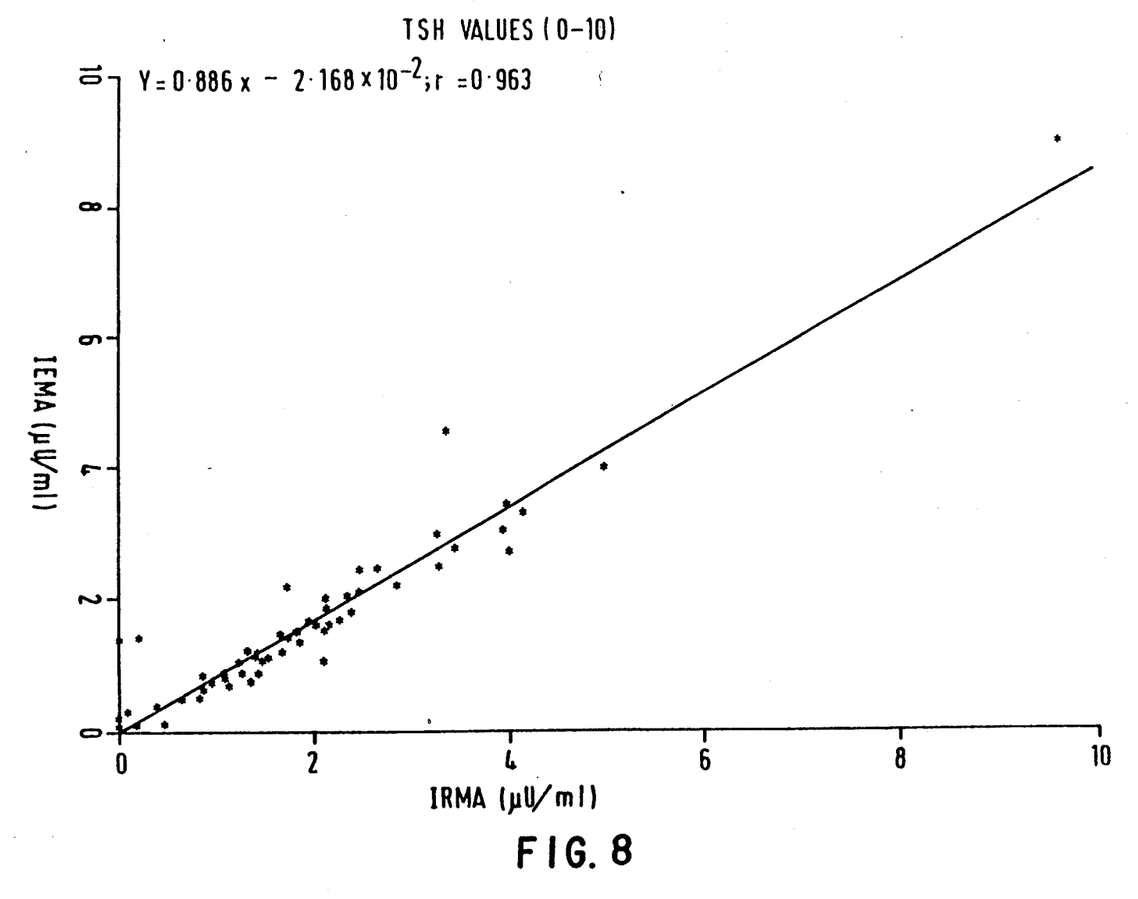
Figure 9:
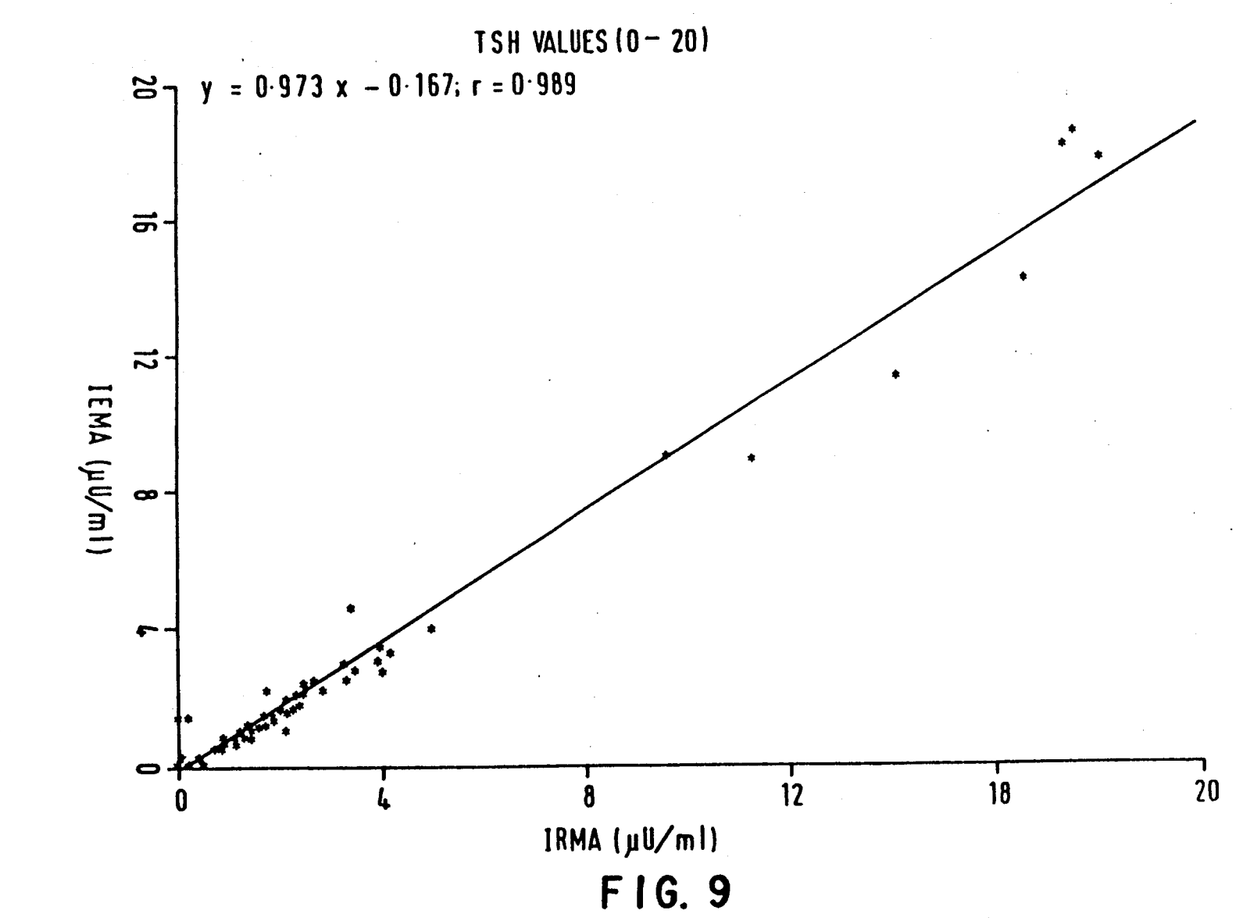

FIG. 7 shows a comparison of the "combo" assay TSH results and IRMA TSH results for all 88 samples. FIGS. 8 and 9 show a comparison of TSH results obtained with the "combo" assay and IRMA assay for 0–10 μU/ml and 0–20 μU/ml samples respectively.

Figure 10:
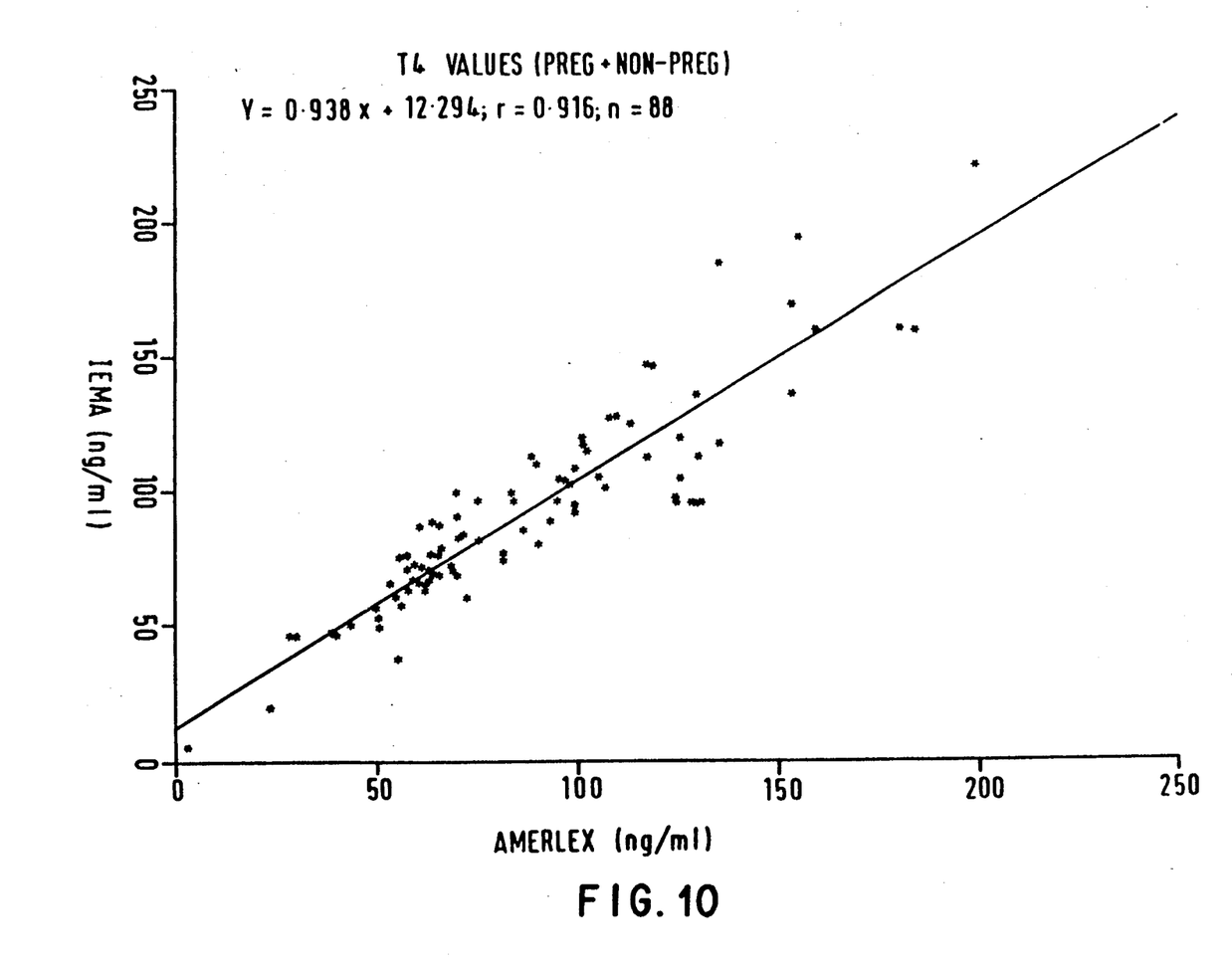
FIG. 10 illustrates a comparison of $T_4$ results determined in accordance with the present invention versus a conventional RIA assay.

A comparison of the $T_4$ values obtained using the "combo" assay and Amerlex $T_4$ RIA kit for all 88 samples is shown in FIG. 10.

We claim:

1. A dual analyte immunoassay process for simultaneously determining first and second analyte ligands present in a liquid sample which comprises:
   (a) incubating the liquid sample simultaneously with at least one alkaline phosphatase labelled antibody specifically bindable to an epitope of the first analyte ligand and at least one β-galactosidase labelled antibody specifically bindable to an epitope of the second analyte ligand so as to form corresponding distinctly labelled antibody-ligand complexes in a liquid phase,
   (b) separating the distinctly labelled antibody-ligand complexes as a solid phase from the liquid phase,
   (c) incubating either the solid phase or the liquid phase simultaneously with both o- or p-nitrophenyl-β-D-galactoside and phenolphthalein monophosphate, and
   (d) simultaneously monitoring the production of o- or p-nitrophenol and phenolphthalein and determining the first and second analyte ligands therefrom.

2. The method of claim 1 wherein step (c) is conducted at a pH between 7 and 10 in the presence of diethanolamine at a concentration of 0.25M to 1M.

3. The method of claim 2 wherein step (c) is conducted at a pH between 8.5 and 8.7.

4. The method of claim 3 wherein step (c) is conducted with 3–10 mM phenolphthalein and about 50 mM p-nitrophenyl-β-D-galactoside.

5. The method of claim 3 wherein the concentration of o- or p-nitrophenyl-β-D-galactoside is sufficient to substantially offset inhibition of β-galactosidase by the diethanolamine.

6. The method of claim 5 wherein the monitoring of step (d) comprises simultaneously measuring absorbance at about 404 nm and about 554 nm.

7. The method of claim 1 wherein the incubation step (a) additionally comprises unlabelled antibodies specifically bindable to a different epitope of the first analyte ligand and unlabelled antibodies specifically bindable to a different epitope of the second analyte ligand, each of said unlabelled antibodies being conjugated to a reagent X which is a hapten, avidin, or biotin, and wherein the solid phase of separating step (b) comprises a specific binding partner for reagent X.

8. The method of claim 7 wherein step (c) is conducted at a pH between 8.5 and 8.7 in the presence of diethanolamine at a concentration of 0.25M to 1M.

9. The method of claim 8 wherein reagent X is FITC and the specific binding partner for reagent X is an anti-FITC antibody.

10. A dual analyte immunoassay process for simultaneously determining first and second analyte ligands present in a liquid sample which comprises:
   (a) incubating the liquid sample simultaneously with a ligand analogue of the first analyte ligand, a ligand analogue of the second analyte ligand, at least one alkaline phosphatase labelled antibody specifically bindable to an epitope of the first analyte ligand and ligand analogue, and at least one β-galactosidase labelled antibody specifically bindable to an epitope of the second analyte ligand and ligand analogue so as to form corresponding distinctly labelled antibody-ligand and antibody-ligand analogue complexes in a liquid phase, (b) separating the distinctly labelled antibody-ligand analogue complexes as a solid phase from the liquid phase, (c) incubating either the solid phase or the liquid phase simultaneously with both o- or p-nitrophenyl-β-d-galactoside and phenolphthalein monophosphate, and (d) simultaneously monitoring the production of o- or p-nitrophenol and phenolphthalein and determining the first and second analyte ligands therefrom.

11. The method of claim 10 wherein step (c) is conducted at a pH between 7 and 10 in the presence of diethanolamine at a concentration of 0.25M to 1M.

12. The method of claim 11 wherein step (c) is conducted at a pH between 8.5 and 8.7.

13. The method of claim 12 wherein step (c) is conducted with 3-10 mM phenolphthalein and about 50 mM p-nitrophenyl-β-D-galactoside.

14. The method of claim 12 wherein the concentration of o- or p-nitrophenyl-β-D-galactoside is sufficient to substantially offset inhibition of β-galactosidase by the diethanolamine.

15. The method of claim 14 wherein the monitoring of step (d) comprises simultaneously measuring absorbance at about 404 nm and about 554 nm.

16. The method of claim 15 wherein each of the ligand analogues is conjugated to a reagent X which is a hapten, avidin, or biotin, and wherein the solid phase of separating step (b) comprises a specific binding partner for reagent X.

17. The method of claim 16 wherein reagent X is FITC and the specific binding partner for reagent X is an anti-FITC antibody.

18. A dual analyte immunoassay process for simultaneously determining first and second analyte ligands present in a liquid sample which comprises:

(a) incubating the liquid sample simultaneously with a ligand analogue of the first analyte ligand, unlabelled antibody specifically bindable to an epitope of the second analyte ligand, at least one first enzyme labelled antibody specifically bindable to an epitope of the first analyte ligand and ligand analogue, and at least one second enzyme labelled antibody specifically bindable to a different epitope of the second analyte ligand, wherein one of said first and second enzyme labels is alkaline phosphatase and the other is β-galactosidase, so as to form corresponding distinctly labelled antibody-ligand, antibody-ligand analogue, and antibody-ligand-unlabelled antibody complexes in a liquid phase, (b) separating the distinctly labelled antibody-ligand analogue and antibody-ligand-unlabelled antibody complexes as a solid phase from the liquid phase, (c) incubating either the solid phase or the liquid phase simultaneously with both o- or p-nitrophenyl-β-D-galactoside and phenolphthalein monophosphate, and (d) simultaneously monitoring the production of o- or p-nitrophenol and phenolphthalein and determining the first and second analyte ligands therefrom.

19. The method of claim 18 wherein step (c) is conducted at a pH between 7 and 10 in the presence of diethanolamine at a concentration of 0.25M to 1M.

20. The method of claim 19 wherein step (c) is conducted at a pH between 8.5 and 8.7.

21. The method of claim 20 wherein step (c) is conducted with 3-10 mM phenolphthalein and about 50 mM p-nitrophenyl-β-D-galactoside.

22. The method of claim 20 wherein the concentration of o- or p-nitrophenyl-β-D-galactoside is sufficient to substantially offset inhibition of β-galactosidase by the diethanolamine.

23. The method of claim 22 wherein the monitoring of step (d) comprises simultaneously measuring absorbance at about 404 nm and about 554 nm.

24. The method of claim 23 wherein each of the ligand analogue and the unlabelled antibody is conjugated to a reagent X which is a hapten, avidin, or biotin, and wherein the solid phase of separating step (b) comprises a specific binding partner for reagent X.

25. The method of claim 24 wherein reagent X is FITC and the specific binding partner for reagent X is anti-FITC antibody.

26. A dual analyte immunoassay reagent kit for the simultaneous assay of first and second analytes present in a liquid sample comprising, as separate kit components:

(a) a reagent solution comprising a mixture of (i) at least one alkaline phosphatase labelled antibody specifically bindable to an epitope of the first analyte ligand, (ii) at least one β-galactosidase labelled antibody specifically bindable to an epitope of the second analyte ligand, (iii) either unlabelled antibody specifically bindable to a different epitope of the first analyte ligand or a ligand analogue to the first analyte ligand, and (iv) either unlabelled antibody specifically bindable to a different epitope of the second analyte ligand or a ligand analogue to the second analyte ligand, each of said unlabelled antibodies or ligand analogues being conjugated to a reagent X wherein X is which is a hapten, avidin, or biotin;

(b) a solid phase support bound to a specific binding partner for reagent X; and (c) a buffered reagent solution comprising a mixture of o- or p-nitrophenyl-β-D-galactoside and phenolphthalein monophosphate.

27. The reagent kit of claim 26 wherein component (c) is at a pH between 8.5 and 8.7.

28. The reagent kit of claim 27 wherein component (c) additionally comprises diethanolamine at a concentration of 0.25M to 1M.

* * * * *